United States Patent [19]
Binet et al.

[11] Patent Number: 5,580,881
[45] Date of Patent: Dec. 3, 1996

[54] 1,2,3,5,6,7,8,8A-OCTAHYDRO-5,5,8A-TRIMETHYL-(8Aβ)-6-ISOQUINOLINEAMINE DERIVATIVES, PREPARATION METHOD THEREFOR AND THERAPEUTICAL USE THEREOF

[75] Inventors: Jean Binet, Fontaine les Dijon; Soth Samreth, Longvic; Daniel De Fornel; Thierry Boucher, both of Dijon; Patrice Renaut, Hauteville-les-Dijon, all of France

[73] Assignee: Fournier Industrie Et Sante, France

[21] Appl. No.: 424,419

[22] PCT Filed: Oct. 18, 1993

[86] PCT No.: PCT/FR93/01022

§ 371 Date: Apr. 27, 1995

§ 102(e) Date: Apr. 27, 1995

[87] PCT Pub. No.: WO94/10150

PCT Pub. Date: May 11, 1994

[30] Foreign Application Priority Data

Oct. 28, 1992 [FR] France .................................. 92 12865

[51] Int. Cl.$^6$ ...................... C07D 217/02; C07D 217/04; C07D 405/06; A61K 31/47
[52] U.S. Cl. ........................ 514/307; 546/139; 546/146; 546/149

[58] Field of Search ..................... 546/139, 146, 546/149, 307; 514/307

[56] References Cited

U.S. PATENT DOCUMENTS

| 4,863,932 | 9/1989 | Jinensky ................................... 514/307 |
| 5,084,461 | 1/1992 | Wannamaker et al. .................. 514/307 |

FOREIGN PATENT DOCUMENTS 8908450   9/1989   WIPO .................................... 514/307

*Primary Examiner*—Zinna Northington Davis
*Attorney, Agent, or Firm*—Ostrolenk, Faber, Gerb & Soffen, LLP

[57] ABSTRACT

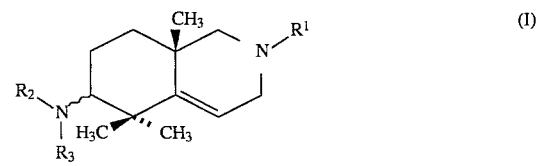

1,2,3,5,6,7,8,8a-Octahydro-5,5,8a-trimethyl-(8aβ)-isoquinolineamines of formula (I), wherein groups $R^1$–$R^3$ are as defined in the description, a method for preparing same, and therapeutical uses thereof as agents for inhibiting the biosynthesis of cholesterol, particularly epoxysqualene cyclase, which are useful as cholesterol and lipid lowering drugs, antiatheromatic and antifungal agents.

25 Claims, No Drawings

5,580,881

1,2,3,5,6,7,8,8A-OCTAHYDRO-5,5,8A-TRIMETHYL-(8Aβ)-6-ISOQUINOLINEAMINE DERIVATIVES, PREPARATION METHOD THEREFOR AND THERAPEUTICAL USE THEREOF

This application is a 371 of PCT/FR/01022 filed Oct. 18, 1993.

BACKGROUND OF THE INVENTION

The present invention relates to 1,2,3,5,6,7,8,8a-octahydro-5,5,8a-trimethyl-(8aβ)-6-isoquinolineamine derivatives, which inhibit the biosynthesis of cholesterol, and especially of epoxysqualene cyclase, in mammals and fungi, to their method of preparation and to their use in therapeutics as hypocholesterolemics, hypolipidemics, antiatheromatous agents and antifungal agents.

Various compounds which inhibit the different enzymes involved in the biosynthesis of cholesterol, and especially of squalene epoxidase and epoxysqualene cyclase, are already known.

Numerous studies have stressed the importance and advantage of these products in the normalization of the cholesterol level and in the antifungal sphere by virtue of their capacity to inhibit the biosynthesis of ergosterol.

For example, patent application EP-A-468434 describes 4-hydroxypiperidine ethers or thioethers which inhibit epoxysqualene cyclase.

Likewise, patent applications EP-A-468457 and EP-A-420116 describe β-methyl-4-piperidineethanol derivatives and alkyl-4-piperidinol compounds as squalene epoxidase inhibitors, said derivatives and compounds being useful as antiatheromatous agents and antifungal agents.

These compounds also include decalin and azadecalin derivatives such as those described for example in international patent application WO-A-89/08450 and patent U.S. Pat. No. A-5084461, which are useful as hypocholesterolemics and antifungal agents.

None of these documents of the prior art either describes or suggests 1,2,3,5,6,7,8,8a-octahydro-5,5,8a-trimethyl-(8aβ)-6-isoquinolineamine derivatives useful as inhibitors of the biosynthesis of cholesterol, and especially of epoxysqualene cyclase.

SUMMARY OF THE INVENTION

The present invention therefore proposes 1,2,3,5,6,7,8,8a-octahydro-5,5,8a-trimethyl-(8aβ)-6-isoquinolineamine derivatives which inhibit the biosynthesis of cholesterol, and especially of epoxysqualene cyclase.

DESCRIPTION OF THE INVENTION

The present invention relates to the compounds selected from the group consisting of the 1,2,3,5,6,7,8,8a-octahydro-5,5,8a-trimethyl-(8aβ)-6-isoquinolineamines of the formula

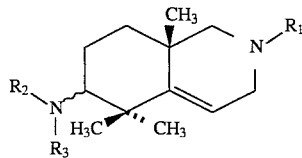

(I)

in which
R$_1$ is:

a linear or branched C$_1$–C$_{12}$-alkyl group optionally substituted by:
 a cycloalkyl group,
 an oxiranyl group, or
 a phenyl group substituted by a C$_1$–C$_4$-alkyl group,
a linear or branched C$_3$–C$_{12}$-alkyl group containing one or more double or triple bonds and optionally substituted by one or two phenyl groups, or
a linear or branched C$_3$–C$_4$-alkyl group substituted by one or more hydroxyl groups, either R$_2$ and R$_3$, which are identical or different, are each a hydrogen atom or a C$_1$–C$_4$-alkyl group, R$_2$ is a hydrogen atom or a C$_1$–C$_4$-alkyl group and R$_3$ is a trifluoroacetyl group or an acetyl group, and the symbol ∼∼∼ is an α- or β-bond in the 6-position, and their addition salts.

Addition salts are understood here as meaning the acid addition salts.

Acid addition salts are understood as meaning the salts obtained with organic acids such as, for example, 4-methylbenzenesulfonic, (E)-2-butenedioic, (Z)-2-butenedioic, ethanedioic and methanesulfonic acids, or with mineral acids such as, for example, hydrochloric, hydrobromic, sulfuric, nitric and phosphoric acids.

C$_1$–C$_{12}$-Alkyl group is understood here as meaning a linear or branched alkyl group containing from 1 to 12 carbon atoms.

The preferred alkyl groups are the n-propyl, methyl, 2-methylethyl, 2-methylpropyl and dodecyl groups.

The preferred C$_1$–C$_{12}$-alkyl groups containing one or more double or triple bonds are the 2-propen-1-yl, 6,6-dimethylhept-2-en-4-yn-1-yl, 3-methyl-2-buten-1-yl, 3-phenyl-2-propen-1-yl and 3,3-diphenyl-2-propen-1-yl groups.

The 2,3-dihydroxypropyl group is the preferred group among the linear or branched C$_3$–C$_4$-alkyl groups containing from 3 to 4 carbon atoms and substituted by one or more hydroxyl groups.

Cycloalkyl group is understood here as meaning a cyclic alkyl group containing from 3 to 6 carbon atoms; the preferred cycloalkyl group according to the invention is cyclopropane.

According to the invention, the following compounds are preferred:
N-trifluoroacetyl-1,2,3,5,6,7,8,8a-octahydro-2-(2-propen-1-yl)-5,5,8a-trimethyl-(6β,8aβ)-6-isoquinolineamine
N,N-dimethyl-1,2,3,5,6,7,8,8a-octahydro-2-dodecyl-5,5,8a-trimethyl-(6β,8aβ)-6-isoquinolineamine (E)-2-butenedioate
N,N-dimethyl-1,2,3,5,6,7,8,8a-octahydro-2-(3-phenyl-2-propen-1-yl)-5,5,8a-trimethyl-(6β,8aβ)-6-isoquinolineamine 4-methylbenzenesulfonate
N,N-dimethyl-1,2,3,5,6,7,8,8a-octahydro-2-[2-methyl-3-[4-(1-methylethyl)phenyl]propyl]-5,5,8a-trimethyl-(6β,8aβ)-6-isoquinolineamine (E)-2-butenedioate.

The compounds of formula I according to the invention can be prepared by a method characterized in that:
i) a compound of the formula

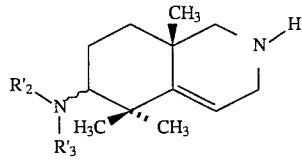

(II)

in which the symbol ∼∼∼ is an α-bond or a β-bond in the 6-position and either R'$_2$ and R'$_3$, which are identical or different, are a C$_1$–C$_4$-alkyl group, or R'$_2$ is a hydrogen atom and R'$_3$ is a trifluoroacetyl group, is N-alkylated by reaction with a compound of the formula R'$_1$—X in which X is a halogen atom such as, for example, a bromine or chlorine atom, and R'$_1$ is defined in the same way as R$_1$ in formula I, in the presence or absence of a polar or non-polar and aprotic solvent such as, for example, acetonitrile or N,N-dimethylformamide, in the presence or absence of an alkali metal salt such as, for example, potassium carbonate, at a rate of one mol of compound of formula II to 1.1 to 1.2 mol of compound of the formula R'$_1$—X at a temperature between room temperature and 150° C. and for at least one hour, to give a compound of the formula

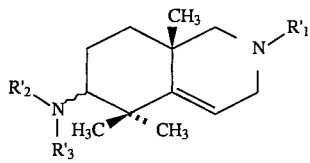 (I')

in which R'$_2$, R'$_3$ and R'$_1$ are as defined above and the symbol ∿ is an α-bond or a β-bond in the 6-position; and ii) if necessary, the resulting compounds of formula I' are subjected to at least one of the following treatments:

a) the compounds of formula I' in which R'$_1$ is as defined above, R'$_2$ is a hydrogen atom, R'$_3$ is a trifluoroacetyl group and the symbol ∿ is an α-bond or a β-bond in the 6-position are converted, by alkylation of the amide in the 6-position according to the methods known to those skilled in the art, especially in the presence of a strong base such as, for example, sodium hydride, at a rate of one mol of compound of formula I' per mol of hydride, at a temperature of between 20° and 60° C., for at least one hour, followed by reaction with a C$_1$–C$_4$-alkyl halide such as, for example, methyl iodide, in the presence of an appropriate solvent such as, for example, N,N-dimethylformamide, at a rate of 1 mol of compound of formula I' to 1.2 mol of alkyl halide, at a temperature near room temperature and for a few hours to several days, into compounds of formula I in which R$_1$ is as defined above, R$_2$ is a C$_1$–C$_4$-alkyl group, R$_3$ is a trifluoroacetyl group and the symbol ∿ is an α-bond or a β-bond in the 6-position;

b) the trifluoroacetyl group carried by the amine in the 6-position of the compounds of formula I' in which R'$_1$ is as defined above, R'$_3$ is a trifluoroacetyl group and R'$_2$ is a hydrogen atom or a C$_1$–C$_4$-alkyl group is removed by hydrolysis according to the methods known to those skilled in the art, especially in the presence of an alkali metal salt such as, for example, potassium carbonate, in an alcohol such as, for example, methanol, in the presence of water, at a rate of one mol of compound I' to a large excess of alkali metal salt, at a temperature between room temperature and 200° C. and for a few hours to several days, to give the compounds of formula I in which R$_1$ is as defined above, R$_3$ is a hydrogen atom, R$_2$ is a hydrogen atom or a C$_1$–C$_4$-alkyl group and the symbol ∿ is an α-bond or a β-bond in the 6-position;

c) the compounds obtained in b) are acylated according to the methods known to those skilled in the art, especially by reaction with an acid anhydride such as, for example, acetic anhydride, in an appropriate solvent such as, for example, tetrahydrofuran, in the presence or absence of N,N-diethylethanamine, to give the compounds of formula I in which R$_3$ is an acyl group, R$_2$ is a hydrogen atom or a C$_1$–C$_4$-alkyl group, the symbol ∿ is an α-bond or a β-bond in the 6-position and R$_1$ is as defined above, with the exception of the compounds of formula I in which R$_1$ is a linear or branched C$_3$–C$_4$-alkyl group substituted by one or more hydroxyl groups, or else a linear or branched C$_1$–C$_{12}$-alkyl group substituted by an oxiranyl group; or d) the compounds obtained in b) in which R$_2$ and R$_3$ are both a hydrogen atom are converted, by reductive alkylation according to the methods known to those skilled in the art, especially by reaction with an appropriate compound of the formula R$_4$—CHO, in which R$_4$ is a hydrogen atom or a C$_1$–C$_3$-alkyl group, such as, for example, formaldehyde, followed by adjustment of the pH to between 6 and 8 and reduction of the iminium ion formed, in the presence of an appropriate reducing agent such as, for example, sodium cyanotriborohydride, for a few hours to several days, into compounds of formula I in which R$_2$ and R$_3$, which are identical or different, are each a C$_1$–C$_4$-alkyl group, R$_1$ is as defined above and the symbol ∿ is either an α-bond or a β-bond in the 6-position.

In another method according to the invention, the compounds of formula I' in which R'$_1$ is as defined above and R'$_2$ and R'$_3$, which are identical or different, are each a C$_1$–C$_4$-alkyl group are obtained by N-alkylation of the compounds of formula II in which R'$_2$ and R'$_3$, which are identical or different, are a C$_1$–C$_4$-alkyl group and the symbol ∿ is an α-bond or a β-bond in the 6-position, by means of reductive amination by reaction with a carbonyl derivative of the formula R"$_1$—CH=O in which R"$_1$ is chosen so as to give the desired group R'$_1$ by the addition of one carbon relative to R"$_1$ after reduction of the iminium ion formed, according to the methods known to those skilled in the art, especially in the presence of an appropriate reducing agent such as, for example, sodium cyanotriborohydride, at room temperature, for one hour to several days, at a rate of 1 mol of compound of formula II to 1.1 to 1.2 mol of compound of the formula R"$_1$ CH=O.

In another synthetic method according to the invention, the compounds of formula I' in which R'$_1$ is as defined above, R'$_2$ and R'$_3$ which are identical or different, are each a C$_1$–C$_4$-alkyl group and the symbol ∿ is an α-bond or a β-bond in the 6-position can also be obtained according to the methods known to those skilled in the art, especially by N-acylation of the compounds of formula II in which R'$_2$ and R'$_3$, which are identical or different, are a C$_1$–C$_4$-alkyl group and the symbol ∿ is an α-bond or a β-bond in the 6-position with an acid or an appropriate acid derivative such as, for example, an acid halide, followed by reduction in the presence of a reducing agent such as, for example, sodium bis(2-methoxyethoxy)aluminum hydride, for at least one hour.

To obtain the compounds of formula II in which either R'$_2$ and R'$_3$ which are identical or different, are each a C$_1$–C$_4$-alkyl group, or R'$_2$ is a hydrogen atom and R'$_3$ is a trifluoroacetyl group, and the symbol ∿ is an α- or β-bond in the 6-position, it is recommended in a first step to prepare 2-phenylmethyl-8a-methyl-1,3,4,7,8,8a-hexahydro-6(2H)-isoquinolinone by means of a condensation reaction, according to the methods known to those skilled in the art, between 1-phenylmethyl-3-methyl-4-piperidone and methyl vinyl ketone in the presence of a strong base such as, for example, sodium methylate, and then to convert said isoquinolinone by reaction with a large excess of a compound of the formula X—COO—R$_5$, in which X is a halogen atom such as, for example, a chlorine atom and R$_5$ is a phenylmethyl group or a C$_1$–C$_4$-alkyl group, according to the methods known to those skilled in the art, especially in a chlorinated solvent such as, for example, chloroform, at a temperature of between 25° and 200° C., for several hours, to give a compound of the formula

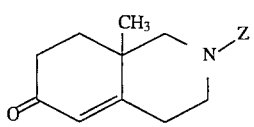

(III)

in which Z is a protective group such as, for example, a group COOR$_5$, in which R$_5$ is a phenylmethyl group or a C$_1$–C$_4$-alkyl group.

The compounds of formula III are then alkylated in the 5-position according to the methods known to those skilled in the art, especially by reaction with a methyl halide such as, for example, methyl iodide, in an alcohol such as, for example, 1,1-dimethylethanol, in the presence of the potassium salt of 1,1-dimethylethanol, at a temperature of between 20° and 150° C., for several hours, to give the compounds of the formula

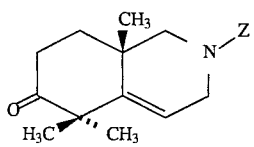

(IV)

in which Z is as defined above. The carbonyl in the 6-position is then subjected to reductive amination according to the methods known to those skilled in the art, especially by reaction with an appropriate aminated derivative which may or may not be in the form of a salt, such as, for example, ammonium acetate, in an alcohol such as, for example, methanol, and reduction with an appropriate reducing agent such as, for example, sodium cyanotriborohydride, at room temperature, for a few hours to several days, to give a compound of the formula

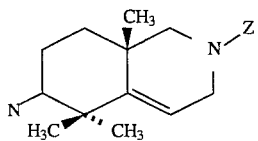

(V)

in which Z is as defined above.

The compounds of formula V are then acylated according to the methods known to those skilled in the art, especially by reaction with trifluoroacetic anhydride in an appropriate solvent such as, for example, tetrahydrofuran, in the presence or absence of N,N-dimethylethanamine, to give the compounds of the formula

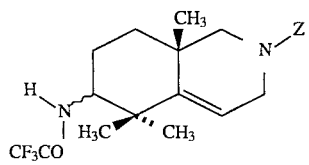

(VI)

in which Z is as defined above, and the 6α and 6β isomers are separated according to the methods known to those skilled in the art, especially by chromatography on a silica column.

The compounds of formula II in which R'$_2$ is a hydrogen atom and R'$_3$ is a trifluoroacetyl group are then obtained directly in the form of the α or β isomer by deprotection of the cyclic amine of formula VI in which Z is a group COOR$_5$ in which R$_5$ is a phenylmethyl group, according to the methods known to those skilled in the art, especially by hydrogenolysis under a hydrogen atmosphere, in the presence of a catalyst such as, for example, palladium-on-charcoal, in an alcohol such as, for example, ethanol.

The compounds of formula II in which R'$_2$ or R'$_3$, which are identical or different, are a C$_1$–C$_4$-alkyl group are obtained in the following manner:

In a first step, the trifluoroacetyl group of the α or β isomers of the compounds of formula VI, in which Z is as defined above, is hydrolyzed according to the methods known to those skilled in the art, especially by reaction with an alkali metal salt such as, for example, potassium carbonate, in an alcohol, in the presence of water, to give the compounds of the formula

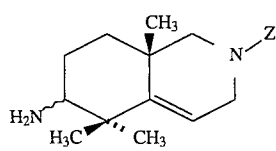

(V')

in which Z is a protective group such as, for example, a group COOR$_5$, in which R$_5$ is a phenylmethyl group or a C$_1$–C$_4$-alkyl group, and the symbol ⌇ is an α-bond or a β-bond in the 6-position.

In a second step, the compounds of formula V' are converted by means of reductive alkylation according to the methods known to those skilled in the art, especially by reaction with an appropriate carbonyl derivative such as, for example, formaldehyde, followed by reduction with an appropriate reducing agent such as, for example, sodium cyanotriborohydride, to give the compounds of the formula

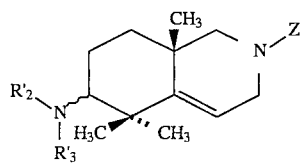

(VIII)

in which Z is as defined above, the symbol ⌇ is an α-bond or a β-bond in the 6-position and R'$_2$ and R'$_3$, which are identical or different, are each a C$_1$–C$_4$-alkyl group.

Finally, in a third step, the compounds of formula VII are deprotected by removal of the group Z according to the methods known to those skilled in the art, especially by hydrogenolysis in the presence of a catalyst such as, for example, palladium-on-charcoal, if Z is a group COOR$_5$ in which R$_5$ is a phenylmethyl group, or by reaction with a silyl derivative such as, for example, trimethylsilyl chloride, in the presence of sodium iodide, for several hours, at a temperature of between 20° and 200° C., if Z is a group COOR$_5$ in which R$_5$ is a C$_1$–C$_4$-alkyl group, to give the desired compounds of formula II.

The intermediates of formula II in which the symbol ⌇ is an α-bond or a β-bond in the 6-position and either R'$_2$ and R'$_3$ which are identical or different, are each a C$_1$–C$_4$-alkyl group, or R'$_2$ is a hydrogen atom and R'$_3$ is a trifluoroacetyl group, are novel compounds and form one of the subjects of the invention.

The intermediates of formula VI in which the symbol ⌇ is an α-bond or a β-bond in the 6-position and Z is a protective group such as, for example, a group COOR$_5$, in which R$_5$ is a phenylmethyl group or a C$_1$–C$_4$-alkyl group, are novel compounds and form one of the subjects of the invention.

The intermediates of formulae III, IV, V and V' in which Z is a protective group such as, for example, a group COOR$_5$, in which R$_5$ is a phenylmethyl group or a C$_1$–C$_4$-alkyl group, are novel compounds.

The intermediates of formula VII in which the symbol ⌇ is an α-bond or a β-bond in the 6-position, Z is a protective group such as, for example, a group COOR$_5$, in which R$_5$ is a phenylmethyl group or a C$_1$–C$_4$-alkyl group, and R'$_2$ and R'$_3$ which are identical or different, are each a C$_1$–C$_4$-alkyl group are novel compounds.

The invention will be understood more clearly from the Preparatory Examples below. These Examples are intended to illustrate the invention without limiting its scope. For convenience, in the text which follows, the "Preparations" refer to the preparation of the precursors and intermediates, and the "Examples" refer to the preparation of the products of formula I according to the invention.

PREPARATION I

2-Phenylmethyl-8a-methyl-1,3,4,7,8,8a-hexahydro-6(2H)-isoquinolinone 101.5 g ($5.10^{-1}$ mol) of 1-phenylmethyl-3-methyl-4-piperidone are added to a solution of sodium methylate prepared beforehand from 12.7 g ($5.5.10^{-1}$ mol) of sodium in one liter of methanol.

The mixture is stirred for 45 minutes at room temperature, the solution is cooled to 5° C. and 62.3 ml ($7.5.10^{-1}$ mol) of methyl vinyl ketone are added dropwise in about 2 hours.

The mixture is allowed to return to 20° C. and left to stand overnight. 55 ml of concentrated hydrochloric acid are added and the mixture is evaporated to dryness. The residue is taken up with 1,1'-oxybisethane and water. The organic phase is washed with water, dried over magnesium sulfate and filtered and the solvents are evaporated off under reduced pressure.

The oil obtained is purified by chromatography on a silica column using a dichloromethane/2,2'-oxybispropane mixture (9/1 v/v) as the eluent to give 37.8 g (yield: 30%) of the desired product, which crystallizes from n-pentane.

M.p.=98° C.

PREPARATION II

Phenylmethyl 2,3,4,6,7,8-hexahydro-8a-methyl-6-oxo-2(1H)-isoquinolinecarboxylate A mixture of 35 g ($1.4.10^{-1}$ mol) of 2-(phenylmethyl)-8a-methyl-1,3,4,7,8,8a-hexahydro-6(2H)-isoquinolinone and 99 ml ($7.10^{-2}$ mol) of phenylmethyl chloroformate in 300 ml of chloroform is refluxed overnight in the presence of 28.6 g ($2.10^{-2}$ mol) of potassium carbonate. The mixture is cooled and filtered, the filtrate is washed with water and dried and the solvents are evaporated off under reduced pressure.

The recovered residual oil is triturated in petroleum ether to give 36 g (yield: 87%) of the desired product.

M.p.=128° C.

The product below is obtained by following the same procedure except that ethyl chloroformate is used as the starting material:
ethyl 2,3,4,6,7,8-hexahydro-8a-methyl-6-oxo-2(1H)-isoquinolinecarboxylate.
M.p.=66°–69° C.

PREPARATION III

Phenylmethyl 3,5,6,7,8,8a-hexahydro-5,5,8a-trimethyl-6-oxo-(8aβ)-2(1H)-isoquinolinecarboxylate 35 g ($1.2.10^{-1}$ mol) of phenylmethyl 2,3,4,6,7,8-hexahydro-8a-methyl-6-oxo-2(1H)-isoquinolinecarboxylate are solubilized in 350 ml of 1,1-dimethylethanol. 39.4 g ($3.5.10^{-1}$ mol) of the potassium salt of 1,1-dimethylethanol are then added all at once.

The mixture turns red. It is stirred for 1 hour at 50° C. and a solution of 44.3 ml ($7.10^{-1}$ mol) of iodomethane in 1,1-dimethylethanol is cautiously added dropwise in 30 minutes. A yellow precipitate appears. When the addition is complete, the mixture is heated at 50° C. for 1 hour and then stirred overnight at room temperature. The mixture is poured into water and extracted with ethyl acetate. The organic phase is washed with water, dried over magnesium sulfate and filtered and the solvents are evaporated off under reduced pressure.

After purification by chromatography on a silica column using a methylbenzene/ethyl acetate mixture (9/1 v/v) as the eluent, 23.6 g (yield: 62%) of the desired product are recovered in the form of a slightly yellow oil.

$n_D^{31}$=1.5375

The product below is obtained by following an analogous procedure using ethyl 2,3,4,6,7,8-hexahydro-8a-methyl-6-oxo-2(1H)-isoquinolinecarboxylate as the starting material:
ethyl 3,5,6,7,8,8a-hexahydro-5,5,8a-trimethyl-6-oxo-(8aβ)-2(1H)-isoquinolinecarboxylate.
M.p.=58° C.

PREPARATION IV

Phenylmethyl 3,5,6,7,8,8a-hexahydro-5,5,8a-trimethyl-6-amino-(8aβ)-2(1H)-isoquinolinecarboxylate A solution of 65 g ($2.10^{-1}$ mol) of phenylmethyl 3,5,6,7,8,8a-hexahydro-5,5,8a-trimethyl-6-oxo-(8aβ)-2(1H)-isoquinolinecarboxylate in 700 ml of methanol is mixed with 153 g (2 mol) of ammonium acetate, the pH of the solution is adjusted to 7.3 by the addition of acetic acid, and 20 g ($3.10^{-1}$ mol) of sodium cyanotriborohydride are then added in portions.

The solution is stirred for 2 days at room temperature. The methanol is evaporated off, the evaporation residue is taken up with a solution of sodium hydroxide and extraction is carried out with ethyl acetate.

The organic phase is washed with water, dried over magnesium sulfate and filtered and the solvents are evaporated off under reduced pressure.

The recovered oil is solubilized in 5N hydrochloric acid and extraction is carried out with 1,1'-oxybisethane.

The aqueous phase is rendered alkaline with a solution of sodium hydroxide and extraction is carried out with ethyl acetate.

The organic phase is washed with water, dried over magnesium sulfate and filtered and the solvents are evaporated off under reduced pressure.

This gives 52 g (yield: 80%) of the desired product in the form of a yellow oil.

$n_D^{34}$=1.5469

The product below is obtained by following an analogous procedure using ethyl 3,5,6,7,8,8a-hexahydro-5,5,8a-trimethyl-6-oxo-(8aβ)-2(1H)-isoquinolinecarboxylate as the starting material:
ethyl 3,5,6,7,8,8a-hexahydro-5,5,8a-trimethyl-6-amino-(8aβ)-2(1H)-isoquinolinecarboxylate (E)-2-butenedioate.
M.p.=140°–145° C.

PREPARATION V

Phenylmethyl 3,5,6,7,8,8a-hexahydro-5,5,8a-trimethyl-6-(trifluoroacetylamino)-(8aβ)-2(1H)-isoquinolinecarboxylate 50 g (1.5.10$^{-1}$ mol) of phenylmethyl 3,5,6,7,8,8a-hexahydro-5,5,8a-trimethyl-6-amino-(8aβ)-2(1H)-isoquinolinecarboxylate are solubilized in 200 ml of tetrahydrofuran and 25.5 ml of N,N-diethylethanamine. The solution is cooled to about 0° C. and a solution of 25.8 ml (1.8.10$^{-1}$ mol) of trifluoroacetic anhydride in 50 ml of tetrahydrofuran is added dropwise.

The reaction mixture is stirred overnight at room temperature. It is evaporated under reduced pressure and the residual oil is taken up with 1,1'-oxybisethane.

The organic phase is washed with a 1N solution of hydrochloric acid and then with water, dried over magnesium sulfate and filtered and the solvents are evaporated off under reduced pressure to give the desired compound in the form of an oil.

After purification of the resulting oil by chromatography on a silica column using a 2,2'-oxybispropane/methylcyclohexane mixture (9/1 v/v) as the eluent, 6.5 g (yield: 12%) of the following product are recovered:
phenylmethyl 3,5,6,7,8,8a-hexahydro-5,5,8a-trimethyl-6-(trifluoroacetylamino)-(6α,8aβ)-2(1H)-isoquinolinecarboxylate
$n_D^{36}$=1.5145
and 37.1 g (yield: 59%) of the following product are recovered:
phenylmethyl 3,5,6,7,8,8a-hexahydro-5,5,8a-trimethyl-6-(trifluoroacetylamino)-(6β,8aβ)-2(1H)-isoquinolinecarboxylate.
M.p.=138° C.

The 2 isomers below are obtained, after purification, by following an analogous procedure using ethyl 3,5,6,7,8,8a-hexahydro-5,5,8a-trimethyl-6-amino-(8aβ)-2(1H)-isoquinolinecarboxylate as the starting material:
ethyl 3,5,6,7,8,8a-hexahydro-5,5,8a-trimethyl-6-(trifluoroacetylamino)-(6α,8aβ)-2(1H)-isoquinolinecarboxylate.
$n_D^{32}$=1.4845
ethyl 3,5,6,7,8,8a-hexahydro-5,5,8a-trimethyl-6-(trifluoroacetylamino)-(6β,8aβ)-2(1H)-isoquinolinecarboxylate.
M.p.=70°–80° C.

PREPARATION VI

N-Trifluoroacetyl-1,2,3,5,6,7,8,8a-octahydro-5,5,8a-trimethyl-(6β,8aβ)-6-isoquinolineamine 4-methylbenzenesulfonate A solution of 27 g (6.10$^{-2}$ mol) of phenylmethyl 3,5,6,7,8,8a-hexahydro-5,5,8a-trimethyl-6-(trifluoroacetylamino)-(6β,8aβ)-2(1H)-isoquinolinecarboxylate in 150 ml of ethanol is hydrogenated under atmospheric pressure, at room temperature, in the presence of 2.7 g of 5% palladium-on-charcoal.

When the reaction has ended, the reaction mixture is filtered, the catalyst is removed and the filtrate is evaporated to dryness.

After trituration of the recovered residue in 2,2'-oxybispropane, 16.5 g (yield: 90%) of a product melting at 154° C. are obtained, from which the 4-methylbenzenesulfonate is prepared in ethanol.
M.p.>260° C.

The product below is prepared by following an analogous procedure using the (6α,8aβ) isomer of phenylmethyl 3,5,6,7,8,8a-hexahydro-5,5,8a-trimethyl-6-(trifluoroacetylamino)-2(1H)-isoquinolinecarboxylate as the starting material:
N-trifluoroacetyl-1,2,3,5,6,7,8,8a-octahydro-5,5,8a-trimethyl-(6α,8aβ)-isoquinolineamine.
$n_D^{31}$=1.4902

EXAMPLE 1

N-Trifluoroacetyl-1,2,3,5,6,7,8,8a-octahydro-2-(2-propen-1-yl)-5,5,8a-trimethyl-(6β,8aβ)-6-isoquinolineamine A solution of 0.7 ml (8.10$^{-1}$ mol) of 3-bromo-1,2-propene in 2 ml of acetonitrile is added dropwise to a mixture of 2 g (7.10$^{-3}$ mol) of N-trifluoroacetyl-1,2,3,5,6,7,8,8a-octahydro-5,5,8a-trimethyl-(6β,8aβ)-6-isoquinolineamine and 1.9 g of anhydrous potassium carbonate in 60 ml of acetonitrile.

After refluxing for one hour, the precipitate is filtered off, the filtrate is evaporated to dryness and the residual oil is taken up with water. Extraction is carried out with 1,1'-oxybisethane. The organic phase is dried over magnesium sulfate and filtered and the solvents are evaporated off under reduced pressure.

The oil recovered in this way is purified by chromatography on a silica column using a dichloromethane/methanol mixture (98/2 v/v) as the eluent to give 2 g (yield: 91%) of a white product.
M.p.=130° C.

The compounds below are prepared by following a procedure analogous to the above synthesis:

EXAMPLE 2

N-Trifluoroacetyl-1,2,3,5,6,7,8,8a-octahydro-2-propyl-5,5,8a-trimethyl-(6β,8aβ)-6-isoquinolineamine M.p.=105°–108° C.

EXAMPLE 3

N-Trifluoroacetyl-1,2,3,5,6,7,8,8a-octahydro-2-(cyclopropylmethyl)-5,5,8a-trimethyl-(6β,8aβ)-6-isoquinolineamine (E) -2-butenedioate M.p.=193°–197° C.

EXAMPLE 4

N-Trifluoroacetyl-1,2,3,5,6,7,8,8a-octahydro-2-(6,6-dimethyl-2-hepten-4-yn-1-yl)-5,5,8a-trimethyl-(6β,8aβ)-6-isoquinolineamine M.p.=131° C.

EXAMPLE 5

N-Trifluoroacetyl-1,2,3,5,6,7,8,8a-octahydro-2-[1-(2,3-epoxypropyl)]-5,5,8a-trimethyl-(6β,8aβ)-6-isoquinolineamine M.p.=130° C.

EXAMPLE 6

N-Trifluoroacetyl-1,2,3,5,6,7,8,8a-octahydro-2-[1-(2,3-dihydroxypropyl)]-5,5,8a-trimethyl-(6β,8aβ)-6-isoquinolineamine E-2-butenedioate M.p.=186° C.

EXAMPLE 7

N-Trifluoroacetyl-1,2,3,5,6,7,8,8a-octahydro-2-(3-methyl-2-buten-1-yl)-5,5,8a-trimethyl-(6β,8aβ)-6-isoquinolineamine ethanedioate M.p.=230° C.

EXAMPLE 8

N-Trifluoroacetyl-1,2,3,5,6,7,8,8a-octahydro-2-dodecyl-5,5,8a-trimethyl-(6β,8aβ)-6-isoquinolineamine M.p.=80° C.

EXAMPLE 9

N-Trifluoroacetyl-1,2,3,5,6,7,8,8a-octahydro-2-(2-propen-1-yl)-5,5,8a-trimethyl-(6β,8aβ)-6-isoquinolineamine M.p.=76° C.

EXAMPLE 10

N-Methyl-N-trifluoroacetyl-1,2,3,5,6,7,8,8a-octahydro-2-dodecyl-5,5,8a-trimethyl-(6β,8aβ)-6-isoquinolineamine A solution of 3.5 g ($1.1.10^{-2}$ mol) of N-trifluoroacetyl-1,2,3,5,6,7,8,8a-octahydro-2-dodecyl-5,5,8a-trimethyl-(6β,8aβ)-6-isoquinolineamine in 20 ml of N,N-dimethylformamide is added to a suspension of 0.43 g ($1.3.10^{-2}$ mol) of 60% sodium hydride in 10 ml of N,N-dimethylformamide.

When the addition is complete, the mixture is heated at 40° C. for one hour. It is cooled, 0.8 ml of iodomethane ($1.3.10^{-2}$ mol) is added and the reaction mixture is stirred for two days at room temperature. It is poured into water and extracted with 1,1'-oxybisethane. The organic phase is washed with water, dried over magnesium sulfate and filtered and the solvents are evaporated off under reduced pressure to give 1.7 g (yield: 47%) of the desired product.

M.p.=132° C.

The compound below is prepared by following a procedure analogous to the above synthesis:

EXAMPLE 11

N-Methyl-N-trifluoroacetyl-1,2,3,5,6,7,8,8a-octahydro-2-(2-propen-1-yl)-5,5,8a-trimethyl-(6β,8aβ)-6-isoquinolineamine M.p.=80° C.

EXAMPLE 12

N-Methyl-1,2,3,5,6,7,8,8a-octahydro-2-dodecyl-5,5,8a-trimethyl-(6β,8aβ)-6-isoquinolineamine ethanedioate A mixture of 2.5 g ($5.10^{-3}$ mol) of N-trifluoroacetyl-N-methyl-1,2,3,5,6,7,8,8a-octahydro-2-dodecyl-5,5,8a-trimethyl-(6β,8aβ)-6-isoquinolineamine and 14.6 g ($10.10^{-2}$ mol) of potassium carbonate in 200 ml of methanol and 50 ml of water is refluxed for 48 hours.

The methanol is evaporated off, the evaporation residue is taken up with water and extraction is carried out with chloroform.

The organic phase is washed with water, dried over magnesium sulfate and filtered and the solvents are evaporated off under reduced pressure.

An oil is recovered which is purified by chromatography on a silica column using a dichloromethane/methanol/aqueous ammonia mixture (98.5/1/0.5 v/v/v) as the eluent.

This gives 1.5 g (yield=79%) of an oil, from which the desired ethanedioate is prepared.

M.p.=134° C.

The compounds below are prepared by following a procedure analogous to the above synthesis:

EXAMPLE 13

N-Methyl-1,2,3,5,6,7,8,8a-octahydro-2-(2-propen-1-yl)-5,5,8a-trimethyl-(6β,8aβ)-6-isoquinolineamine ethanedioate M.p.=180° C.

EXAMPLE 14

1,2,3,5,6,7,8,8a-Octahydro-2-dodecyl-5,5,8a-trimethyl-(6β,8aβ)-6-isoquinolineamine E-2-butenedioate M.p.=155° C.

Starting material: N-trifluoroacetyl-1,2,3,5,6,7,8,8a-octahydro-2-dodecyl-5,5,8a-trimethyl-(6β,8aβ)-6isoquinolineamine.

EXAMPLE 15

1,2,3,5,6,7,8,8a-Octahydro-2-(2-propen-1-yl)-5,5,8a-trimethyl-(6β,8aβ)-6-isoquinolineamine 4-methylbenzenesulfonate M.p.=148° C.

Starting material: N-trifluoroacetyl-1,2,3,5,6,7,8,8a-octahydro-2-(2-propen-1-yl)-5,5,8a-trimethyl-(6β,8aβ)-6-isoquinolineamine.

EXAMPLE 16

N-Acetyl-1,2,3,5,6,7,8,8a-octahydro-2-(2-propen-1-yl)-5,5,8a-trimethyl-(6β,8aβ)-6-isoquinolineamine 4-methylbenzenesulfonate 0.73 ml ($7.8.10^{-3}$ mol) of acetic anhydride diluted in 5 ml of tetrahydrofuran is added dropwise to a solution of 1.5 g ($6.4.10^{-3}$ mol) of 1,2,3,5,6,7,8,8a-octahydro-2-(2-propen-1-yl)-5,5,8a-trimethyl-(6β,8aβ)-6-isoquinolineamine in 20 ml of tetrahydrofuran and 1.1 ml of N,N-diethylethanamine.

The reaction mixture is stirred for 4 hours and then poured into water and extracted with 1,1'-oxybisethane. The organic phase is washed with water, dried over magnesium sulfate and filtered and the solvents are evaporated off under reduced pressure. The oil obtained is purified by chromatography on a silica column using a dichloromethane/methanol mixture (95/5 v/v) as the eluent.

After evaporation of the solvents from the purified fractions, 1 g of an oil is recovered, from which the 4-methylbenzenesulfonate is prepared in 2-propanone. Recrystallization from a butanone/2-propanol mixture (98/2 v/v) gives 1 g (yield: 35%) of the desired product.

M.p.=224° C.

PREPARATION VII

Phenylmethyl 3,5,6,7,8,8a-hexahydro-5,5,8a-trimethyl-6-amino-[6β,8aβ]-2(1H)-isooquinolinecarboxylate A mixture of 35 g ($8.10^{-2}$ mol) of phenylmethyl 3,5,6,7,8,8a-hexahydro-5,5,8a-trimethyl-6-(trifluoroacetylamino)-(6β,8aβ)-2(1H)-isoquinolinecarboxylate in 500 ml of methanol and 100 ml of water with 115 g ($8.10^{-1}$ mol) of potassium carbonate is refluxed for 8 hours.

After evaporation of the reaction mixture, the recovered residue is taken up with water and extracted with ethyl acetate. The organic phase is washed with water, dried over magnesium sulfate and filtered and the solvents are evaporated off under reduced pressure to give 27 g (yield: 100%) of the desired product.

$n_D^{24.5}$=1.5523

The product below is obtained by following the same procedure using the (6α,8aβ) isomer of phenylmethyl 3,5,6,7,8,8a-hexahydro-5,5,8a-trimethyl-6-(trifluoroacetylamino)-2(1H)-isoquinolinecarboxylate as the starting material:
phenylmethyl 3,5,6,7,8,8a-hexahydro-5,5,8a-trimethyl-6-amino-(6α,8aβ)-2(1H)-isoquinolinecarboxylate.
$n_D^{28}$=1.5121

PREPARATION VIII

Phenylmethyl 3,5,6,7,8,8a-hexahydro-5,5,8a-trimethyl-6-dimethylamino-(6β,8aβ)-2(1H)-isoquinolinecarboxylate 27 g ($8.10^{-2}$ mol) of phenylmethyl 3,5,6,7,8,8a-hexahydro-5,5,8a-trimethyl-6-amino-(6β,8aβ)-2(1H)-isoquinolinecarboxylate in 500 ml of acetonitrile are mixed with 74 ml of a 37% aqueous solution of formaldehyde. The mixture is stirred for 10 minutes at about zero degrees and the pH is adjusted to 7.5 by the addition of acetic acid. 15.5 g ($2.5.10^{-1}$ mol) of sodium cyanotriborohydride are then added in portions and the reaction mixture is stirred for 12 hours at room temperature.

After evaporation, the residue obtained is taken up with a solution of sodium hydroxide and extracted with ethyl acetate. The organic phase is washed with water, dried over magnesium sulfate and filtered and the solvents are evaporated off under reduced pressure.

After purification of the recovered residual oil by chromatography on a silica column using a dichloromethane/methanol/aqueous ammonia mixture (8.5/1/0.5 v/v/v) as the eluent, 23.5 g (yield: 80%) of an oil are obtained, which is used in the crude state.

$n_D^{24.5}$=1.5358

The compounds below are prepared by following a procedure analogous to the above synthesis:
ethyl 3,5,6,7,8,8a-hexahydro-5,5,8a-trimethyl-6-dimethylamino-(6α,8aβ)-2(1H)-isoquinolinecarboxylate
$n_D^{29}$=1.5051
ethyl 3,5,6,7,8,8a-hexahydro-5,5,8a-trimethyl-6-dimethylamino-(6β,8aβ)-2(1H)-isoquinolinecarboxylate.
M.p.=54° C.

The compounds below are similarly prepared using the (6β,8aβ) isomer (Example 8) and the (6α,8aβ) isomer of 1,2,3,5,6,7,8,8a-octahydro-2-dodecyl-5,5,8a-trimethyl-6-isoquinolineamine as the starting materials:

EXAMPLE 17

N,N-Dimethyl-1,2,3,5,6,7,8,8a-octahydro-2-dodecyl-5,5,8a-trimethyl-(6β,8aβ)-6-isoquinolineamine (E)-2-butenedioate M.p.=180° C.

EXAMPLE 18

N,N-Dimethyl-1,2,3,5,6,7,8,8a-octahydro-2-dodecyl-5,5,8a-trimethyl-(6α,8aβ)-6-isoquinolineamine ethanedioate M.p.=121°–129° C.

PREPARATION IX

N,N-Dimethyl-1,2,3,5,6,7,8,8a-octahydro-5,5,8a-trimethyl-(6α,8aβ)-6-isoquinolineamine 0.8 g ($2.7.10^{-3}$ mol) of ethyl 3,5,6,7,8,8a-hexahydro-5,5,8a-trimethyl-6-dimethylamino-(6β,8aβ)-2(1H)-isoquinolinecarboxylate is solubilized in 15 ml of acetonitrile and 2.6 g of sodium iodide. 2 ml of trimethylsilyl chloride are added slowly and the reaction mixture is refluxed overnight. A further 2.6 g of sodium iodide and then 2 ml of trimethylsilyl chloride are added and the mixture is refluxed again for 24 hours.

After evaporation under reduced pressure, the residue is taken up with a 1N solution of hydrochloric acid and extracted with 1,1'-oxybisethane. The aqueous phase is rendered alkaline with a solution of sodium hydroxide and extracted with 1,1'-oxybisethane. The organic phase is washed with water, dried over magnesium sulfate and filtered and the solvents are evaporated off under reduced pressure to give 0.5 g (yield: 77%) of the desired product.

M.p.=103° C.

PREPARATION X

N,N-Dimethyl-1,2,3,5,6,7,8,8a-octahydro-5,5,8a-trimethyl-(6β,8aβ)-6-isoquinolineamine A solution of 21.5 g ($6.10^{-2}$ mol) of phenylmethyl 3,5,6,7,8,8a-hexahydro-6-dimethylamino-5,5,8a-trimethyl-(6β,8aβ)-2(1H)-isoquinolinecarboxylate in 250 ml of acetic acid is hydrogenated under atmospheric pressure, at room temperature, in the presence of 3.5 g of 5% palladium-on-charcoal. When the reaction has ended, the catalyst is filtered off and the filtrate is evaporated to dryness.

The residual oil obtained is taken up with water, rendered alkaline with a solution of sodium hydroxide and extracted with 1,1'-oxybisethane.

The organic phase is washed with water, dried over magnesium sulfate and filtered and the solvents are evaporated off under reduced pressure.

12.6 g (yield: 95%) of the desired product are recovered.
M.p.=92° C.

EXAMPLE 19

N,N-Dimethyl-1,2,3,5,6,7,8,8a-octahydro-2-(6,6-dimethyl-2-hepten-4-yn-1-yl)-5,5,8a-trimethyl-(6β,8aβ)-6-isoquinolineamine A solution of 3.8 g ($1.9.10^{-2}$ mol) of 1-bromo-6,6-dimethyl-2-hepten-4-yne (E/Z=3/1) in 20 ml of acetonitrile is added dropwise to a mixture of 3.5 g ($1.6.10^{-2}$ mol) of N,N-dimethyl-1,2,3,5,6,7,8,8a-octahydro-5,5,8a-trimethyl-(6β,8aβ)-6-isoquinolineamine and 2.6 g ($1.9.10^{-2}$ mol) of potassium carbonate in 40 ml of acetonitrile.

When the addition is complete, the reaction mixture is stirred for 2 hours and then poured into water and extracted with ethyl acetate. The organic phase is washed with water, dried over magnesium sulfate and filtered and the solvents are evaporated off under reduced pressure.

After purification on a silica column using 1',1'-oxybisethane as the eluent, 2.8 g (yield: 52%) of the desired product are recovered in the form of a pale yellow oil.

$n_D^{23}$=1.5191

The compounds below are prepared by following a procedure analogous to the above synthesis:

EXAMPLE 20

N,N-Dimethyl-1,2,3,5,6,7,8,8a-octahydro-2-(2-propen-1-yl)-5,5,8a-trimethyl-(6β,8aβ)-6-isoquinolineamine (E)-2-butenedioate M.p.=176° C.

EXAMPLE 21

N,N-Dimethyl-1,2,3,5,6,7,8,8a-octahydro-2-propyl-5,5,8a-trimethyl-(6β,8aβ)-6-isoquinolineamine ethanedioate M.p.=123°–145° C.

EXAMPLE 17

N,N-Dimethyl-1,2,3,5,6,7,8,8a-octahydro-2-dodecyl-5,5,8a-trimethyl-(6β,8aβ)-6-isoquinolineamine (E)-2-butenedioate M.p.=180° C.

EXAMPLE 18

N,N-Dimethyl-1,2,3,5,6,7,8,8a-octahydro-2-dodecyl-5,5,8a-trimethyl-(6α,8aβ)-6-isoquinolineamine ethanedioate M.p.=121°–129° C.

EXAMPLE 22

N,N-Dimethyl-1,2,3,5,6,7,8,8a-octahydro-2-[1-(2,3-dihydroxypropyl)]-5,5,8a-trimethyl-(6β,8aβ)-6-isoquinolineamine M.p.=74° C.

EXAMPLE 23

N,N-Dimethyl-1,2,3,5,6,7,8,8a-octahydro-2-(3-phenyl-2-propen-1-yl)-5,5,8a-trimethyl-(6β,8aβ)-6-isoquinolineamine 4-methylbenzenesulfonate 2.6 g ($1.6.10^{-2}$ mol) of 1,1'-carbonylbis-1H-imidazole are added to a solution of 0.4 g ($1.6.10^{-2}$ mol) of 3-phenyl-2-propenoic acid in 50 ml of tetrahydrofuran and the mixture is stirred for half an hour at room temperature and then for about 1 hour at 50° C. The solution is cooled to 0° C. and a solution of 3 g ($1.3.10^{-2}$ mol) of N,N-dimethyl-1,2,3,5,6,7,8,8a-octahydro-5,5,8a-trimethyl-(6β,8aβ)-6-isoquinolineamine in 40 ml of tetrahydrofuran is added. The reaction mixture is stirred overnight at room temperature and then poured into water and extracted with 1,1'-oxybisethane. The organic phase is washed with water, dried over magnesium sulfate and filtered and the solvents are evaporated off under reduced pressure.

The recovered product is purified by chromatography on a silica column using a dichloromethane/methanol/aqueous ammonia mixture (98.5/1/0.5 v/v/v) as the eluent. 2.8 g (yield: 60%) of an oil are collected, which is used in the crude state in the next step.

1.5 g ($4.2.10^{-3}$ mol) of the above oil are solubilized in 30 ml of methylbenzene, 2.5 ml of 70% sodium bis(2-methoxyethoxy)aluminum hydride in methylbenzene are then added dropwise and this mixture is stirred for 2 and a half hours at room temperature. It is cooled to about 0° C. and a 5N solution of sodium hydroxide is added. After stirring for half an hour, extraction is carried out with 1,1'-oxybisethane. The organic phase is washed with water, dried over magnesium sulfate and filtered and the solvents are evaporated off under reduced pressure.

An oil is recovered, from which the 4-methylbenzenesulfonate is prepared in 2-propanone.

This gives 1.5 g (yield: 58%) of product after recrystallization from acetonitrile.

M.p.=210° C.

The product below is prepared by following a procedure analogous to the above synthesis:

EXAMPLE 24

N,N-Dimethyl-1,2,3,5,6,7,8,8a-octahydro-2-(3,3-diphenyl-2-propen-1-yl)-5,5,8a-trimethyl-(6β,8aβ)-6isoquinolineamine ethanedioate M.p.=161° C.

EXAMPLE 25

N,N-Dimethyl-1,2,3,5,6,7,8,8a-octahydro-2-[1-[2-methyl-3-[4-(1-methylethyl)phenyl]propyl]]-5,5,8a-trimethyl-(6β,8aβ)-6-isoquinolineamine (E)-2-butenedioate 2.8 g ($1.5.10^{-2}$ mol) of 2-methyl-3-[4-(1methylethyl)phenyl]propanal and 2 g of sodium sulfate are added to a solution of 3 g ($1.3.10^{-2}$ mol) of N,N-dimethyl-1,2,3,5,6,7,8,8a-octahydro-5,5,8a-trimethyl(6β,8aβ)-6-isoquinolineamine in 100 ml of methanol. After the addition of acetic acid to adjust the pH of the mixture to about 7, 1.3 g ($2.10^{-2}$ mol) of sodium cyanotriborohydride are added and this mixture is stirred overnight at room temperature. After filtration and evaporation of the solvents, the residue is taken up with a normal solution of sodium hydroxide. Extraction is carried out with 1,1'-oxybisethane. The organic phase is washed with water, dried and filtered and the solvents are evaporated off under reduced pressure. The product obtained is purified by chromatography on a silica column using a dichloromethane/methanol/aqueous ammonia mixture (95.5/4/0.5 v/v/v) as the eluent. 2.2 g (yield: 41%) of an oil are collected, from which the desired (E)-2-butenedioate is prepared in 2-propanone.

M.p.=142°–150° C.

A number of compounds according to the invention have been collated in Table I below. The symbols used in this Table have the following meanings:

n—$C_{12}$: —$(CH_2)_{11}$—$CH_3$

A: —$CH_2$—△

B: —$CH_2$—△O

C: —$CH_2$—$CH(CH_3)$—$CH_2$—⟨phenyl⟩—$CH(CH_3)_2$

D: —$CH_2$—$CH$=$CH$—⟨phenyl⟩

E: —$CH_2$—$CH$=$C$(⟨phenyl⟩)⟨phenyl⟩

F: —$CH_2$—$CH$=$CH$—$C$≡$C$—$C(CH_3)_3$

The symbols used for the salts have the following meanings:
Oxal: $HO_2C$—$CO_2H$
Fum: $HO_2C$—$CH$=$CH$—$CO_2H$ (E)

TSO$_3$H: $CH_3$—⟨phenyl⟩—$SO_3H$

Base: compound in the form of the base

TABLE I

| Ex. | R$_1$ | R$_2$ | R$_3$ | Salt |
|---|---|---|---|---|
| 1 | —$CH_2$—$CH$=$CH_2$ | H | $CF_3CO$ | Base |
| 2 | —$CH_2$—$CH_2$—$CH_3$ | H | $CF_3CO$ | Base |
| 3 | A | H | $CF_3CO$ | Fum |
| 4 | F | H | $CF_3CO$ | Base |
| 5 | B | H | $CF_3CO$ | Base |
| 6 | —$CH_2$—$CH(OH)$—$CH_2$—OH | H | $CF_3CO$ | Fum |
| 7 | —$CH_2$—$CH$=$C(CH_3)_2$ | H | $CF_3CO$ | Oxal |
| 8 | n-$C_{12}$ | H | $CF_3CO$ | Base |
| 9* | —$CH_2$—$CH$=$CH_2$ | H | $CF_3CO$ | Base |
| 10 | n-$C_{12}$ | $CH_3$ | $CF_3CO$ | Base |
| 11 | —$CH_2$—$CH$=$CH_2$ | $CH_3$ | $CF_3CO$ | Base |
| 12 | n-$C_{12}$ | $CH_3$ | H | Oxal |
| 13 | —$CH_2$—$CH$=$CH_2$ | $CH_3$ | H | Oxal |
| 14 | n-$C_{12}$ | H | H | Fum |
| 15 | —$CH_2$—$CH$=$CH_2$ | H | H | TSO$_3$H |
| 16 | —$CH_2$—$CH$=$CH_2$ | H | $CH_3CO$ | TSO$_3$H |
| 17 | n-$C_{12}$ | $CH_3$ | $CH_3$ | Fum |
| 18* | n-$C_{12}$ | $CH_3$ | $CH_3$ | Oxal |

TABLE I-continued

| Ex. | R$_1$ | R$_2$ | R$_3$ | Salt |
|---|---|---|---|---|
| 19 | F | $CH_3$ | $CH_3$ | Base |
| 20 | —$CH_2$—$CH$=$CH_2$ | $CH_3$ | $CH_3$ | Fum |
| 21 | —$CH_2$—$CH_2$—$CH_3$ | $CH_3$ | $CH_3$ | Oxal |
| 22 | —$CH_2$—$CH(OH)$—$CH_2$—OH | $CH_3$ | $CH_3$ | Base |
| 23 | D | $CH_3$ | $CH_3$ | TSO$_3$H |
| 24 | E | $CH_3$ | $CH_3$ | Oxal |
| 25 | C | $CH_3$ | $CH_3$ | Fum |

*Compounds with a 6α-bond; all the others have a 6β-bond.

The products according to the invention are inhibitors of the biosynthesis of cholesterol, and especially of epoxysqualene cyclase.

The activity of the compounds according to the invention was evaluated by demonstrating an inhibitory effect on the epoxysqualene cyclase of the hepatic microsomes of male Wistar rats.

The method consists in measuring the lanosterol formed from the R,S-2,3-oxidosqualene by the microsomal enzyme. The enzyme is prepared according to the method described by Ness G. C. (Ness G. C. et al., Biochem. J. (1986), 233,167–172).

Method of Measuring the Epoxysqualene Cyclase Activity

Rat hepatic microsomes are used as the enzyme source. The method consists in measuring the lanosterol formed from the R,S-2,3-oxidosqualene. The R,S-2,3-oxidosqualene, the test products and Tween®80, in the form of organic solutions (2-propanone or sulfinylbismethane) (25 µl), are placed in test tubes and 400 µl of potassium phosphate buffer (0.1M, pH=7.4) are then added. The reaction is initiated by the addition of 100 µl of microsomes. For a final reaction volume of 525 µl, the mixture contains 150 µM of R,S-2,3-oxidosqualene, 0.1% of Tween®80 (to solubilize the R,S-2,3-oxidosqualene) and 250 µg of microsomal proteins. The reaction time is 60 minutes at 37° C. The reaction is stopped by the addition of 300 µl of methanolic potassium hydroxide (7%) and 20 µg of stigmasterol as an internal standard. After saponification at 80° C. for 30 minutes and stirring with a rotary stirrer, the sterols are extracted with 2 ml of hexane.

The lanosterol formed is separated from the R,S-2,3-oxidosqualene, the membrane cholesterol and the stigmasterol by gas chromatography after conversion to trimethylsilyl ethers. The derivatization of the sterols is carried out at 60° C. for 30 minutes after the addition of 25 µl of pyridine and 75 µl of the trimethylsilyl ester of 2,2,2-trifluoro-N-trimethylsilylethanimidic acid containing 1% of trimethylchlorosilane ethers.

After evaporation, the trimethylsilyl ethers are redissolved in 100 µl of hexane. An aliquot of this solution (2 µl) is chromatographed in the gas phase on an OV1 capillary column (0.32 mm, 25 m) under the following conditions: injector temperature=270° C., oven temperature=260° C., detector temperature=300° C., the carrier gas being nitrogen at a pressure of $7.10^4$ Pa.

The potency of the molecules tested is expressed as the percentage inhibition of the amount of lanosterol formed for a concentration of $25.10^{-6}$ mol of test product per liter. The results obtained with a number of compounds according to the invention are collated in Table II.

TABLE II

| Ex. | Percentage inhibition for 25.10$^{-6}$ mol of test product |
| --- | --- |
| 6 | 62 |
| 12 | 65 |
| 13 | 63 |
| 14 | 29 |
| 17 | 100 |
| 18 | 66 |
| 20 | 89 |
| 21 | 100 |
| 22 | 64 |
| 23 | 98 |
| 24 | 92 |
| 25 | 98 |

The activity of the compounds according to the invention was also evaluated by demonstrating their capacity to inhibit the biosynthesis of cholesterol in vivo, and especially the inhibition of hepatic epoxysqualene cyclase in OF1 mice according to the operating protocol described below:

The influence of the molecules on hepatic cholesterogenesis in vivo is tested on male OF1 mice. The animals are conditioned in reverse cycle two weeks before administration of the product.

At T=0 on the day of the experiment, the animals (3 to 6 mice/group) receive by oral administration (gavage) a suspension of the test product in the vehicle (3% gum arabic in water).

At T=1 h, the radioactive precursor (R,S-2-$^{14}$C-mevalonolactone) in a 0.9% aqueous solution of NaCl is injected intraperitoneally [2.5 or 5 µCi/mouse (i.e. 9.25×10$^4$ Bq or 1.85×10$^5$ Bq respectively)].

At T=2 h, the animals are sacrificed by dislocation of the cervix; the livers are removed, rinsed, weighed and frozen in liquid nitrogen before being stored at −20° C.

During the conditioning period and on the day of the experiment, the animals have free access to food and drinking water.

The administration of the test product and the injection of the radioactive precursor take place in the middle of the dark period.

After thawing, the whole liver (or part of the liver) is homogenized in water at 0°–4° C. An aliquot of the homogenate is then saponified in alcoholic potassium hydroxide for 90 minutes at 80° C. The unsaponifiable lipids are then extracted with petroleum ether. The solvent is evaporated off to dryness under a stream of nitrogen and the dry residue is redissolved in a chloroform/methanol mixture (2/1). The products contained in the extract are then separated by chromatography on a thin layer of silica after migration in the system hexane/ethyl acetate (80/20).

The deposition of a standard mixture containing non-radioactive cholesterol, lanosterol, monoepoxysqualene, diepoxysqualene and squalene, together with $^{14}$C-cholesterol, makes it possible to determine the Rf of the compounds which serve as a reference for analysis of the radioactive profile of the unsaponifiable lipids.

The distribution of the radioactivity is analyzed with an automatic linear analyzer. The relative percentage of radioactivity in the C$^{27}$-sterol peak of the control (vehicle) group represents 100% incorporation. Calculation of the influence is based on the ratio of the percentage of radioactivity in the C$^{27}$-sterol peak of the treated group to that of the control group.

This method made it possible to demonstrate an inhibition of the biosynthesis of cholesterol in vivo with certain molecules by measuring the drop in the incorporation of radioactivity in the C$^{27}$-sterol peak which was associated with an increase in radioactivity in the peaks corresponding to the epoxysqualenes, as well as the presence of monoepoxysqualene identified by gas chromatography coupled with a mass spectrometer (GC/MS).

The results obtained with a number of compounds according to the invention are collated in Table III and show that certain molecules in this chemical series are potential inhibitors of the hepatic epoxysqualene cyclase of OF1 mice in vivo.

The products according to the invention are useful in therapeutics in the treatment and prevention of hypercholesterolemia, and especially of the associated phenomena of arterial lesions, such as atherosclerosis, and the mycoses and other parasitic complaints caused by a fungus such as, for example, *Actinomyces mentagrophytes, Candida tropicalis, Candida albicans, Candida glabrata* or *Aspergillus fumigatus*.

According to the invention, a therapeutic composition is recommended which is characterized in that it contains at least one compound of formula I or one of its non-toxic acid addition salts in a therapeutically effective amount, in association with a physiologically acceptable excipient.

The use of the compounds of formula I or one of their non-toxic acid addition salts as epoxysqualene cyclase inhibitors is further recommended for the preparation of a preventive or curative hypocholesterolemic, hypolipidemic, antiatheromatous and/or antifungal drug.

The products of formula I according to the invention and their addition salts are particularly useful in the treatment of DICs (disseminated intravascular coagulations) induced especially by molds such as *Candida albicans* and *Candida glabrata*.

The best mode of carrying out the invention consists in using the products of Examples 1, 17, 23 and 25 as drugs, especially hypocholesterolemic and/or antifungal drugs.

TABLE III

Influence of the compounds of formula I or their salts on the biosynthesis of hepatic cholesterol in male OF1 mice

| Ex. | Dose in mg base/kg | Percentage influence* |
| --- | --- | --- |
| 1 | 50 | −37 |
| 1 | 100 | −82/−70 |
| 5 | 50 | −32 |
| 6 | 100 | −74/−78 |
| 16 | 50 | −14 |
| 17 | 50 | −81/−66 |
| 20 | 50 | −21 |

*influence on the incorporation of radioactivity in the C$_{27}$-sterols

What is claimed is:

1. A 1,2,3,5,6,7,8,8a-octahydro-5,5,8a-trimethyl-(8aβ)-6-isoquinolineamine compound, of the formula in which R$_1$ is:

a linear or branched C$_1$–C$_{12}$-alkyl group optionally substituted by:

a $C_3$–$C_6$-cycloalkyl group,
an oxiranyl group, or
a phenyl group substituted by a $C_1$–$C_4$-alkyl group,
a linear or branched $C_3$–$C_{12}$-alkyl group containing one or more double or triple bonds and optionally substituted by one or two phenyl groups, or
a linear or branched $C_3$–$C_4$-alkyl group substituted by one or more hydroxyl groups, either $R_2$ and $R_3$, which are identical or different, are each a hydrogen atom or a $C_1$–$C_4$-alkyl group, or $R_2$ is a hydrogen atom or a $C_1$–$C_4$-alkyl group and $R_3$ is a trifluoroacetyl group or an acetyl group, and the symbol ⌇ is an α-bond or a β-bond in the 6-position, and or an acid addition salt.

2. A compound according to claim 1 wherein the symbol ⌇ is an α-bond in the 6-position.

3. A compound according to claim 1 wherein the symbol ⌇ is a β-bond in the 6-position.

4. A compound according to claim 1 wherein it corresponds to the nomenclature N-trifluoroacetyl-1,2,3,5,6,7,8,8a-octahydro-2-(2-propen-1-yl)-5,5,8a-trimethyl-(6β,8aβ)-6-isoquinolineamine.

5. A compound according to claim 1 wherein it corresponds to the nomenclature N,N-di-methyl-1,2,3,5,6,7,8,8a-octahydro-2-dodecyl-5,5,8a-trimethyl-(6β,8aβ)-6-isoquinolineamine (E)-2-butenedioate.

6. A compound according to claim 1 wherein it corresponds to the nomenclature N,N-di-methyl-1,2,3,5,6,7,8,8a-octahydro-2-(3-phenyl-2-propen-1-yl)-5,5,8a-trimethyl-(6β,8aβ)-6-isoquinolineamine 4-methylbenzenesulfonate.

7. A compound according to claim 1 wherein it corresponds to the nomenclature N,N-di-methyl-1,2,3,5,6,7,8,8a-octahydro-2-[1-[2-methyl-3-[4-(1-methylethyl)phenyl]propyl]]-5,5,8a-trimethyl-(6β,8aβ)-6-isoquinolineamine (E)-2-butenedioate.

8. A method of preparing a compound of formula I according to claim 1, or one of its acid addition salts, said method comprising the steps wherein:
i) a compound of the formula

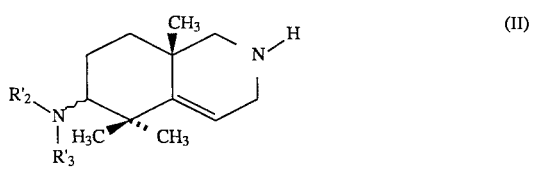

in which the symbol ⌇ is an α-bond or a β-bond in the 6-position and either $R'_2$ and $R'_3$, which are identical or different, are each a $C_1$–$C_4$-alkyl group, or $R'_2$ is a hydrogen atom and $R'_3$ is a trifluoroacetyl group, is N-alkylated by reaction with a compound of the formula $R'_1$—X in which X is a halogen atom and $R'_1$ is defined in the same way as $R_1$ in formula I, at a rate of 1 mol of compound of formula II to 1.1 to 1.2 mol of compounds of the formula $R'_1$—X at a temperature between room temperature and 150° C. and for at least one hour, to give a compound of the formula

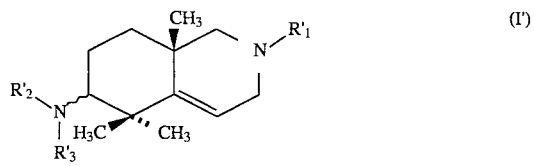

in which $R'_1$, $R'_2$ and $R'_3$ are as defined above and the symbol ⌇ is an α-bond or a β-bond in the 6-position; and
ii) if necessary, the resulting compounds of formula I' are subjected to at least one of the following treatments:

a) the compounds of formula I' in which $R'_1$ is as defined above, the symbol ⌇ is an α-bond or a β-bond in the 6-position, $R'_2$ is a hydrogen atom and $R'_3$ is a trifluoroacetyl group are converted, by alkylation of the amide in the 6-position by reaction with a $C_1$–$C_4$-alkyl halide, in the presence of a strong base, at a rate of one mol of compound of formula I' to 1.2 mol of alkyl halide, at room temperature, into compounds of formula I in which $R_1$ is as defined above, the symbol ⌇ is an α-bond or a β-bond in the 6-position, $R_2$ is a $C_1$–$C_4$-alkyl group and $R_3$ is a trifluoroacetyl group;

b) the trifluoroacetyl group carried by the amine in the 6-position of the compounds of formula I' in which $R'_1$ is as defined above, the symbol ⌇ is an α-bond or a β-bond in the 6-position, $R'_3$ is a trifluoroacetyl group and $R'_2$ is a hydrogen atom or a $C_1$–$C_4$-alkyl group is removed by hydrolysis with an alkali metal salt in an alcohol to give a compound of formula I in which $R_1$ is as defined above, the symbol ⌇ is an α-bond or a β-bond in the 6-position, $R_3$ is a hydrogen atom and $R_2$ is a hydrogen atom or a $C_1$–$C_4$-alkyl group;

c) the compounds obtained in b) are acylated by reaction with an acid anhydride to give the compounds of formula I in which $R_1$ is as defined above, with the exception of the compounds of formula I in which $R_1$ is a linear or branched $C_3$–$C_4$-alkyl group substituted by one or more hydroxyl groups, or else a linear or branched $C_1$–$C_{12}$-alkyl group substituted by an oxiranyl group, $R_3$ is an acyl group, $R_2$ is a hydrogen atom or a $C_1$–$C_4$-alkyl group and the symbol ⌇ is an α-bond or a β-bond in the 6-position; or d) the compounds obtained in b) in which $R_2$ and $R_3$ are both a hydrogen atom are converted, by reductive alkylation with an appropriate carbonyl derivative, followed by reduction of the iminium ion formed with a reducing agent, into compounds of formula I in which $R_2$ and $R_3$, which are identical or different, are each a $C_1$–$C_4$-alkyl group, $R_1$ is as defined above and the symbol ⌇ is either an α-bond or a β-bond in the 6-position.

9. An intermediate compound according to claim 1, of the formula in which the symbol ⌇ is an α-bond or a β-bond in the 6-position and either $R'_2$ is a hydrogen atom and $R'_3$ is a trifluoroacetyl group, or $R'_2$ and $R'_3$ which are identical or different, are each a $C_1$–$C_4$-alkyl group.

10. An intermediate compound according to claim 9, it is a product of the formula in which the symbol ⌇ is an α-bond or a β-bond in the 6-position and Z is a protective group.

11. A pharmaceutical composition comprising a therapeutically effective amount of a compound of claim 1 and a pharmaceutically acceptable carrier.

12. A pharmaceutical composition according to claim 2, comprising a therapeutically effective amount of a compound of claim 1 and a pharmaceutically acceptable carrier.

13. A pharmaceutical composition according to claim 3, comprising a therapeutically effective amount of a compound of claim 1 and a pharmaceutically acceptable carrier.

14. A pharmaceutical composition according to claim 4, comprising a therapeutically effective amount of a compound of claim 1 and a pharmaceutically acceptable carrier.

15. A pharmaceutical composition according to claim 5, comprising a therapeutically effective amount of a compound of claim 1 and a pharmaceutically acceptable carrier.

16. A pharmaceutical composition according to claim 6, comprising a therapeutically effective amount of a compound of claim 1 and a pharmaceutically acceptable carrier.

17. A pharmaceutical composition according to claim 7, comprising a therapeutically effective amount of a compound of claim 1 and a pharmaceutically acceptable carrier.

18. A method of treating hypercholesterolemia, atherosclerosis or mycoses by administering to the patient an effective amount of the compound of claim 1.

19. A method of treating hypercholesterolemia, atherosclerosis or mycoses by administering to the patient an effective amount of the compound of claim 2.

20. A method of treating hypercholesterolemia, atherosclerosis or mycoses by administering to the patient an effective amount of the compound of claim 3.

21. A method of treating hypercholesterolemia, atherosclerosis or mycoses by administering to the patient an effective amount of the compound of claim 4.

22. A method of treating hypercholesterolemia, atherosclerosis or mycoses by administering to the patient an effective amount of the compound of claim 5.

23. A method of treating hypercholesterolemia, atherosclerosis or mycoses by administering to the patient an effective amount of the compound of claim 6.

24. A method of treating hypercholesterolemia, atherosclerosis or mycoses by administering to the patient an effective amount of the compound of claim 7.

25. A compound according to claim 1, in which $R_1$ is selected from the group consisting of n-propyl, methyl, 2-methylethyl, 2-methylpropyl, dodecyl, 2-propen-1-yl, 6,6-dimethylhept-2-en-4-yn-1-yl, 3-methyl-2-buten-1-yl, 3-phenyl-2-propen-1-yl, 3,3-diphenyl-2-propen-1-yl, 2, 3-5-hydroxypropyl and cyclopropyl.

* * * * *